United States Patent [19]

Matsuhiro et al.

[11] Patent Number: 5,625,154

[45] Date of Patent: Apr. 29, 1997

[54] METHOD AND APPARATUS FOR TESTING CERAMIC SPECIMENS BY SIMULTANEOUS APPLICATION OF MECHANICAL AND THERMAL STRESSES

[75] Inventors: Keiji Matsuhiro, Komaki, Japan; Carine A. M. C. Dewitte, Ottignies; Jeffrey P. J. Pattimore, Mons, both of Belgium

[73] Assignees: NGK Ceramics Europe S.A., Belgium; NGK Insulators, Ltd., Japan

[21] Appl. No.: 357,130

[22] Filed: Dec. 15, 1994

[30] Foreign Application Priority Data

Dec. 24, 1993 [GB] United Kingdom .................. 9326472

[51] Int. Cl.$^6$ ............................. G01B 7/16; G01L 1/00
[52] U.S. Cl. ................................. 73/774; 73/760
[58] Field of Search ........................ 73/760, 774, 587, 73/818

[56] References Cited

U.S. PATENT DOCUMENTS

| | | | |
|---|---|---|---|
| 4,099,407 | 7/1978 | Louit | 73/77 |
| 4,277,977 | 7/1981 | Lubitz | 73/587 |
| 4,292,847 | 10/1981 | Tait | 73/587 |
| 4,344,326 | 8/1982 | Kahu | 73/587 |
| 4,559,824 | 12/1985 | Soma et al. | 73/432 |
| 4,562,736 | 1/1986 | Iwasaki et al. | 73/587 |
| 5,101,663 | 4/1992 | Narita et al. | 73/588 |
| 5,237,876 | 8/1993 | Liu | 73/831 |

OTHER PUBLICATIONS

Patent Abstracts of Japan, vol. 7, No. 78 (P–188)—JP–A–58 009043 Jan. 19, 1993.
Patent Abstracts of Japan, vol. 16, No. 82 (M–1215)—JP–A–03 264713 Nov. 26, 1991.

8186 Fusion Technology, 23 (1993) Jul., No. 4, "A New Method To Evaluate The Thermal Shock Resistance of Ceramics By Laser Pulse Irradiation" by S. Akiyama et al. Jul. 1993.

Silicon Nitride Turbocharger Rotor for High Performance Automotive Engines, Tetsuji Shimizu et al., pp. 163–175 No Date.

Thermal Shock Testing of Ceramics—A New Testing Method, Gerold A. Schneider et al., *J. Am. Ceram. Soc.*, 74[1], pp. 98–102 (1991).

Hot–Gas–Jet Method and Apparatus for Thermal–Shock Testing, George C. Wei et al., *J. Am. Ceram. Soc.*, 72[7] pp. 1286–1289 (1989).

Modelling and Measuring of the Thermal Shock Behaviour of Ceramics, W. Pompe et al., *Wissenschafts–Forum Scientific Forum*, cfi/Ber. DKG 70 (1993) No. 3, pp. 79–84.

*Primary Examiner*—Richard Chilcot
*Assistant Examiner*—Max H. Noori
*Attorney, Agent, or Firm*—Parkhurst, Wendel & Burr, L.L.P.

[57] ABSTRACT

A method and apparatus for testing a ceramic member applies mechanical stress to the member by application of mechanical force and simultaneously applies thermal stress by creating a temperature gradient in the member by localized heating of a portion thereof. The mechanical stress is impact stress or may be applied by application of a static load to the ceramic member. The method is especially applied to the proof-testing a plurality of ceramic members for quality assurance, particularly engine valve members.

27 Claims, 5 Drawing Sheets

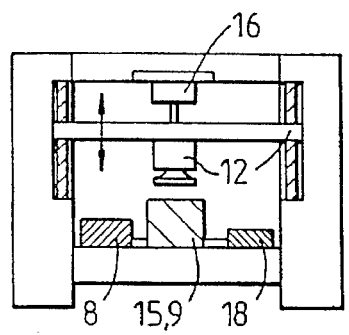
FIG. 3a
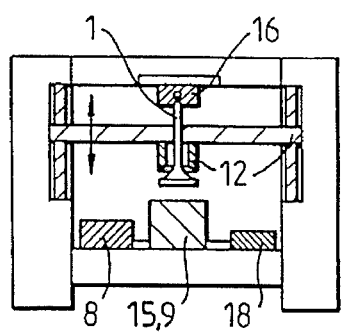
FIG. 3b
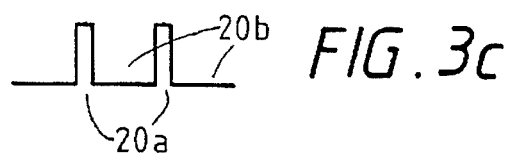
FIG. 3c
FIG. 4
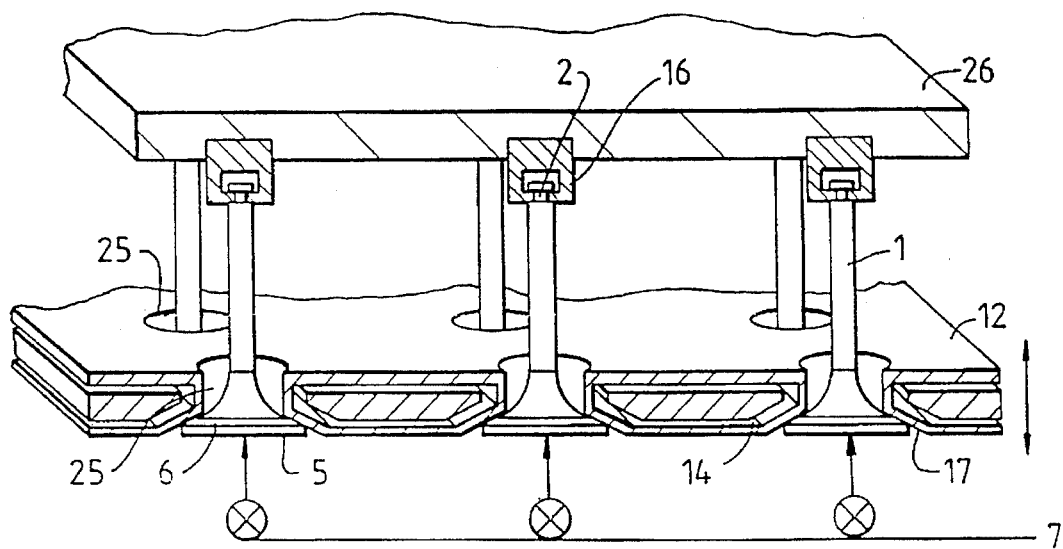

FIG. 5a
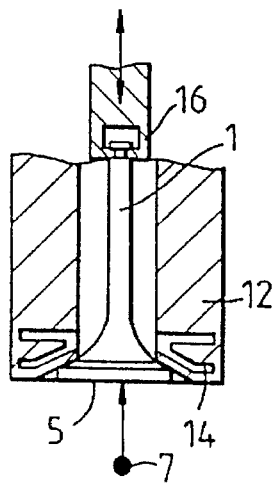
FIG. 5b
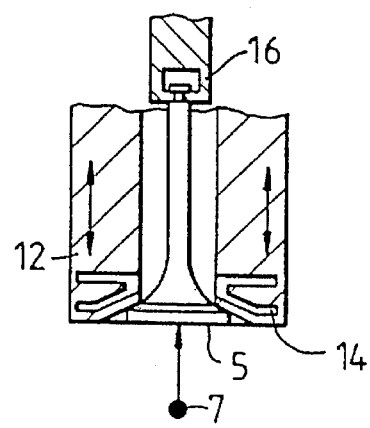
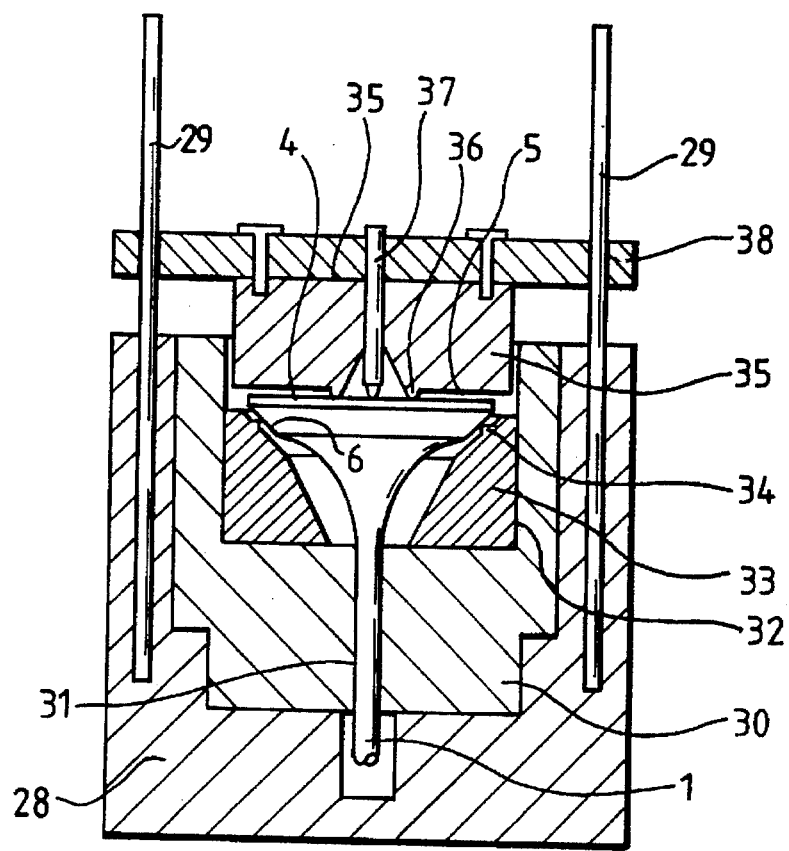
FIG. 6.

METHOD AND APPARATUS FOR TESTING CERAMIC SPECIMENS BY SIMULTANEOUS APPLICATION OF MECHANICAL AND THERMAL STRESSES

BACKGROUND OF THE INVENTION

1. FIELD OF THE INVENTION

The present invention relates to methods and apparatus for testing ceramic members, and particularly to the proof-testing of ceramic members, for example ceramic valve members for engines, for the purposes of quality assurance. Although the invention is particularly described herein in relation to testing of ceramic engine valve members, it is not limited to this application and is generally applicable to ceramic parts and components.

2. DESCRIPTION OF THE PRIOR ART

The use of ceramic components to replace metal parts, for example, in internal combustion engines, is becoming increasingly common. Ceramics provide good wear resistance, strength at high temperatures, and lower mass than metal parts, and their use can reduce friction and fuel consumption. One example is the use of ceramics for engine valve members, which are subjected to severe stresses during operation of the engine when the valve, which is exposed to gases at high temperatures, opens and closes for example 6,000 times per minute. A ceramic material such as silicon nitride can withstand these stresses, but defects may be introduced during the production of the valve member which could lead to failure of the valve in use if they are not detected.

It appears that attention has not yet been paid to the problem of quality assurance of ceramic valve members, or other ceramic parts, which are made by mass production methods. Rigorous quality assurance is required, in order that ceramic components shall reach the same standard of reliability as has become commonplace for components made of metal. Although understanding of the behaviour of ceramic materials is increasing rapidly, it has not reached the same level as that of metal components. Inspection techniques for ceramic materials and components which have been described in the prior art are generally not adapted to quality assurance in mass production. In mass production, the inspection time available may be only a few seconds for each component tested, in order not to slow down the production process. Furthermore, the test should be capable of providing an assurance of quality for the designed working life of the component, which for example is the same as the intended life of an automobile engine in which the component is fitted.

Mechanical testing methods of ceramic materials and components have of course been described, such as bending tests. JP-A-3-13842 describes a rotary bending test and a tensile test for a ceramic valve member. Also described in the prior art are thermal resistance tests, such as a thermal shock test, which involves rapid cooling from high temperature. Spot-heating by lasers or other heat sources has been used to cause crack propagation in test disks. It is also well known to test a ceramic material by subjecting it to mechanical stress while it is maintained at a predetermined temperature.

An article "Silicon nitride turbo-charger rotor for high performance automotive engines" by T. Shimizu et. al., SAE Technical Paper No. 900656, also published in SAE Proceedings No. SP-823, pages 163–175, describes the development and testing of a ceramic turbocharger rotor, including durability testing under conditions more severe and longer than those in actual engines. Proof testing of mass-produced rotors is not discussed.

Methods have also been developed for nondestructive testing of ceramic materials and components, in order to detect small defects. Such techniques are x-ray imaging, ultrasonic scanning and fluorescence dye penetration, but in the testing of mass produced articles, these techniques alone are not practical or are not capable of detecting very small defects, e.g. less than 100 μm in size.

To summarise therefore, conventional testing methods for ceramic materials and components have generally been for the purposes of research, and the requirements of testing for quality assurance in mass production have not been addressed.

SUMMARY OF THE INVENTION

An object of the present invention is to provide a method of testing of a ceramic member which is suitable for providing quality assurance in mass production.

Another object is to provide a method of testing ceramic components to determine their stress limit under specified conditions.

The testing method of the invention subjects the ceramic member, such as a ceramic valve member, simultaneously to both mechanical stress and thermal stress. The thermal stress is applied by creating a temperature gradient within the ceramic member, typically by heating a selected portion or portions of the member. The heating may be by spot heating, such as by a radiation beam, e.g. a laser beam. Cooling may also be performed e.g. by contact with the surface of another member. Both the heating and the cooling may be intermittent or pulsed.

The mechanical stress may be static stress applied by a tool or may be impact stress. Impact stress may be applied once or repeatedly, e.g. by contacting a surface portion of the member with a striker member or by impact applied to an intermediate member contacting the ceramic member. The striker member or intermediate member may be cooled, to apply cooling.

As indicated above, the invention can be applied to limit testing (e.g. destructive testing) of a ceramic component under investigation and to proof-testing of ceramic components after manufacture. In the case of proof-testing, the stresses applied are selected in accordance with the particular component and its intended use; factors to be considered in selecting the stresses are size, material, stresses arising in normal use, intended life-time in use, location of maximum stresses in use, etc.

In the mechanical proof-testing of a component, it is known to apply mechanical stress greater than that expected to be applied during its normal use. As mentioned above, thermal shock testing of ceramic components has been carried out, at least for research purposes. The present inventors however found that the simultaneous application of mechanical stress and thermal stress by creation of a temperature gradient, provides a test for the reliability of the ceramic member in actual use, which subjects the member to conditions different from those of actual use but provides useful assurance that the member will meet the conditions of actual use. Thus preferably at least one of the mechanical stress and thermal stress applied is more severe than expected in normal use of the member, and in particular it is preferred that the temperature gradient is greater than expected in normal use. This particularly applies in the case where the temperature gradient is established by spot heating of a surface portion of the member. In use for example of a ceramic valve member, the head face is not subjected to spot heating, but general heating. Therefore this test does not exactly simulate conditions of use, but is believed to provide a useful test for the purpose of quality assurance.

Thus the present invention can provide a proof-testing method for a ceramic member e.g. a valve member, in which there can be both quantitative change, e.g. increase, from the expected conditions of actual use of the member, as well as a qualitative change from the conditions experienced in use, e.g. a different pattern of thermal stress. The testing method is susceptible of accurate control, and can be repeated rapidly for a large number of components. It is also possible to test a plurality of components simultaneously in a simple apparatus. The test takes place on a test rig, e.g. outside an engine in which the component is used, and it is not necessary for example to simulate flow of hot gases around a valve member. The test can take place in the ambient atmosphere.

The proof-testing method also includes the step of monitoring during and/or after the application of the mechanical and thermal stresses. This monitoring may be by visual inspection, for example, or may be automated. Visual inspection is possible, because a failure of the member, e.g. a valve member, is likely to take the form of a visible chip or crack. Alternatively or additionally, a monitoring apparatus may be employed, such as x-ray imaging, ultrasonic testing or dye testing, to detect defects, e.g. flaws or failures, caused by the applied stresses. Such defects are larger, and therefore easier to detect, than original defects present before testing.

BRIEF INTRODUCTION OF THE DRAWINGS

Embodiments of the invention will now be described, by way of non-limitative example, with reference to the accompanying drawings, in which:

FIG. 3a shows, diagrammatically, one arrangement of apparatus for proof-testing of valve members according to the invention;

FIG. 3b shows the apparatus of FIG. 3a in partial cross-section;

FIG. 3c is a diagrammatic representation of oscillation pattern for the mechanical force applied to the valve member;

FIG. 4 shows a schematic view of an apparatus for proof-testing a plurality of valve members simultaneously;

FIG. 5 shows two possible alternative methods of mechanical force application in the invention;

FIG. 6 is a sectional view of a further apparatus of the invention, for proof-testing of valve members;

Figure 9A:
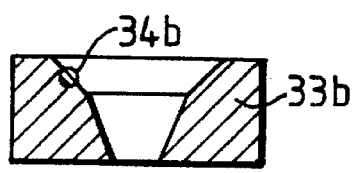
Figure 9B:
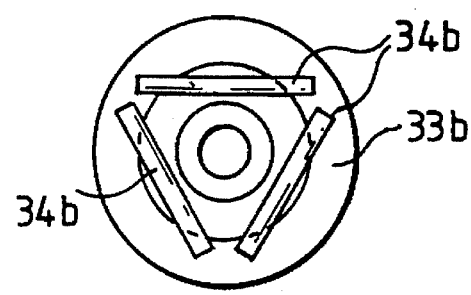
Figure 10:
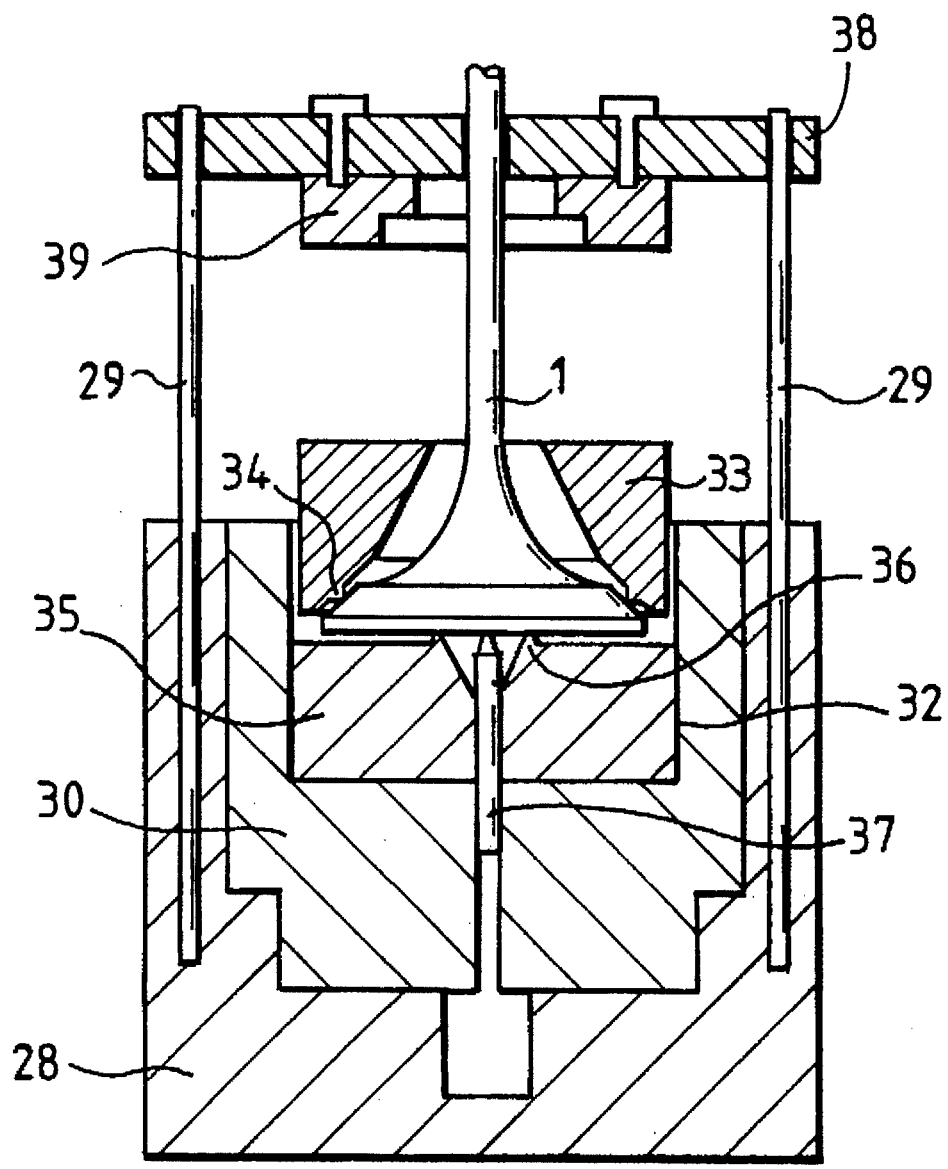

FIGS. 7a and 7b, FIGS. 8a and 8b and FIGS. 9a and 9b are axial sectional views and plan views of three bottom rings for use in the apparatus of FIG. 6; and FIG. 10 is a sectional view of another apparatus, for testing of valve members, in accordance with the invention.

DESCRIPTION OF THE PREFERRED EMBODIMENTS

Figure 1:
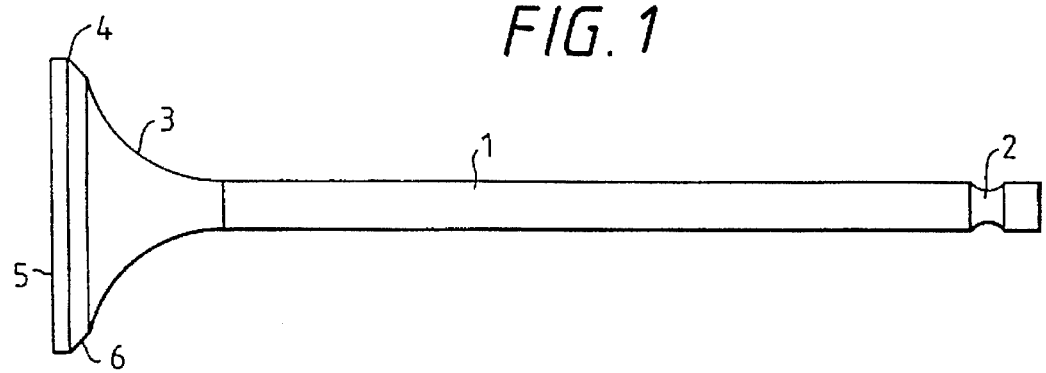
FIG. 1 is a schematic diagram of a known valve member which may be the subject of proof-testing according to the invention.

FIG. 1 shows a typical ceramic valve member for an internal combustion engine which is made in one piece of silicon nitride and has a cylindrical stem 1 with a groove 2 extending round the circumference of the stem 1 at one end. At the other end, the diameter of the stem increases to form a flared, bell-shaped underhead 3 terminating in the head 4 of the valve member. The head 4 comprises the flat head face 5 and a frustoconical annular seating face 6 of the valve member, situated between the head face 5 and the underhead 3. It is the seating face 6 which is in contact with the seat of the valve opening (not shown) in the engine when the valve is closed.

In operation in the engine the valve member is held at the groove 2. As the valve is opened and closed the valve member is pushed out of and into contact with the seat of the valve opening. Contact is made at the seating face 6 of the valve member. The head face 5 is subjected to temperatures which may be over 800° C., but the temperature at the rest of the valve member is lower, so that thermal stresses, especially in the region of the head of the valve member, are great. Mechanical stresses in the same region, and near the groove where the valve member is held, are also high, particularly impact stresses as the valve opens and closes at for example 6000 times per minute.

When proof-testing mass-produced ceramic valve members in one method according to the present invention, each valve member, after grinding to finished shape, is fixed to the testing apparatus by holding means, such as a retainer clamp 16 (FIG. 3), acting at the groove 2. The head face 5 of the valve member is heated by a radiant spot-heating heat source 7, for example a pulsing laser (FIG. 2) such as a Nd-YAG laser, whose beam is directed onto a relatively small area 10 at the centre of the head face 5 by reflectors 15. The other parts of the valve member are cooled by the surrounding air, and the seating face 6 of the valve member is cooled by contact with a cooling block 12 which has a flow of coolant, for example water, within it through internal channels 14 (suitable connections to the channels 14 are not shown). This heating and cooling rapidly establishes a severe temperature gradient between the centre of the head face 5 and the seating face 6 of the valve member.

Figure 2:
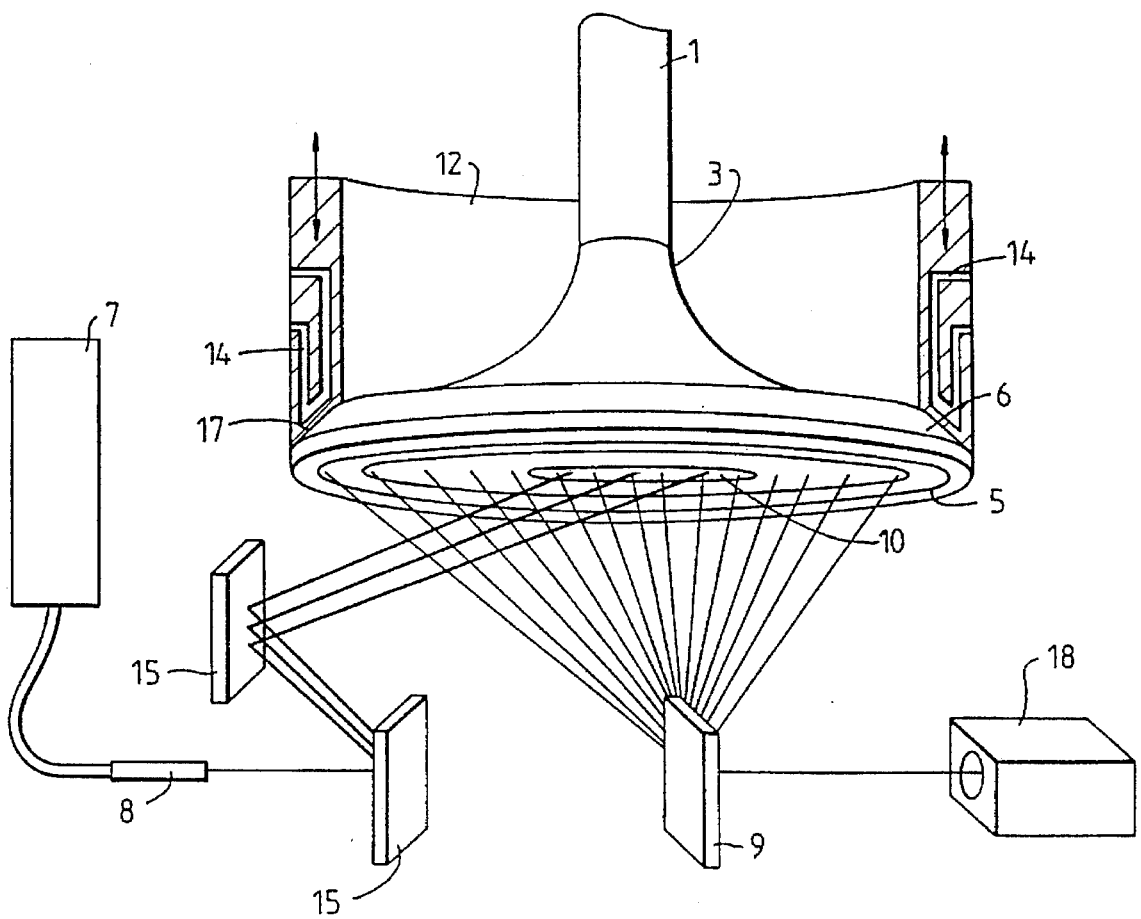
FIG. 2 shows a valve member undergoing proof-testing by a method of the invention.
Figure 7A:
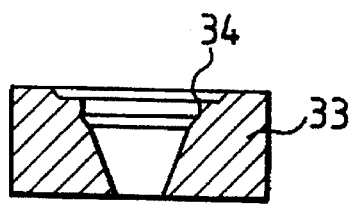
Figure 7B:
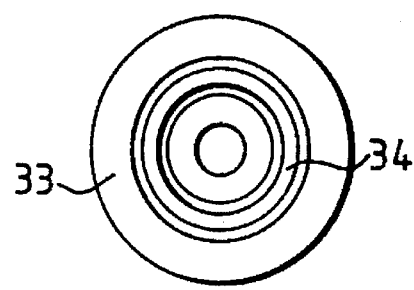
Figure 8A:
Figure 8B:
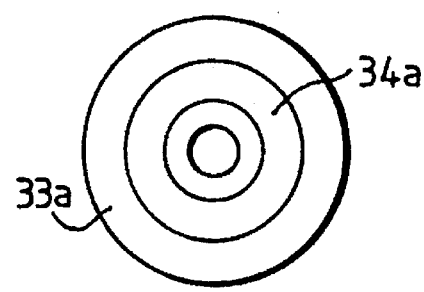

As can be seen in FIG. 2 the cooling block 12 is conically shaped to be able to provide good contact with the seating face 6. The cooling block 12 has an inclined surface 17 to match the angle of the frustoconical seating face 6 of the valve member with which it is brought into contact. The block 12 may be in the form of a ring or tube (FIGS. 2 and 3) or may be a larger block with an aperture 25 (FIG. 4) through which the valve member extends, the periphery of the aperture providing the bevelled cooling surface 17 which is brought into contact with the seating face 6.

The temperature gradient may be monitored by, for example, a pyrometer 18 arranged to scan across the head face 5 using a directable detector 9. This gives an indication of the thermal stress established across the valve member head 4.

The thermal stress may be adjusted by controlling the heating and cooling, for example by changing the intensity of the laser and/or the rate of flow of the coolant. The area heated by the laser may also be adjusted by means of the movable reflectors 15.

The surface 17 of the cooling block 12 which is able to contact the seat 6 of the valve member being tested also delivers force to the valve member to generate rapid oscillating mechanical stress, simultaneously with the heating and cooling described above. The cooling block 12 is movable relative to the head 4 of the valve member and the mechanical stress is generated by repeated impact in a predetermined pattern of force application of the surface 17 on the seating face 6. In one embodiment the valve member is held by the groove 2, suspended from the clamp 16 (see FIG. 3), and the cooling block 12 is raised and lowered, rapidly, in a predetermined pattern of shorter non-contact periods 20a and longer contact periods 20b (FIG. 3c), to simulate repeated opening and closing of the valve in use. In an alternative embodiment the cooling block 12 is held stationary and the clamp 16, from which the valve. member depends, is rapidly raised and lowered to bring the seat 6 of the valve member repeatedly into contact with the surface 17. These two alternative modes are illustrated in FIG. 5. A high number of impacts per second is preferred, to simulate conditions in an engine.

FIG. 4 shows an apparatus for proof-testing a plurality of valve members at one time. The valve members are each clamped by clamps 16 to the apparatus at the grooves 2 of their stems and extend through apertures 25 in the large cooling block 12. The peripheries of the apertures 25 are shaped to provide cooling force application surfaces 17 able to form a good contact with the seating faces 6 of the valve members. The block 12 is moved rapidly up and down to impact repeatedly with all the valve members simultaneously. Alternatively the clamps 16, fixed to common base unit 26, may be moved simultaneously to bring the valve members into contact with the stationary cooling block 12. The head faces 5 may be heated by a single heat source 7 directed to each valve member individually, for example using a laser whose beam has been split, or separate heat sources 7 may be provided.

After the application of mechanical and thermal stress as illustrated, the proof-testing is completed by inspection monitoring to detect valve members which have failed in the test. Suitable inspection methods are described above.

The apparatus shown in FIGS. 2 to 5 is capable of adjustment to give the desired test characteristics; for example, the following are adjustable, laser power, laser spot size, laser pulse rate, mechanical force and oscillation pattern, cooling water flow rate.

The proof-testing method illustrated here can be performed quickly, since the cyclic impact mechanical stress, e.g. higher than expected in use of the valve member in an engine, can be applied rapidly and the laser spot heating allows rapid creation of the desired temperature gradient. The desired location of both mechanical and thermal stresses is achieved precisely.

Instead of a laser, other heat sources for spot heating may be used, such as a flame, a hot gas jet or a focused heating lamp, e.g. a halogen lamp.

The testing method and apparatus described above applies mechanical stress to all parts of the valve member, and thermal stress to the valve head 4. This is useful for providing an overall proof test of the valve member. However experience of failure of valve members in simulated and actual use suggests that of particular interest is the application of mechanical stress to the region of the seat face 6. FIGS. 6 to 9 show an apparatus for applying static load to the valve head, in particular to the seat face 6, and thermal stress to the valve head 4, without applying stress to the valve stem 1.

The apparatus of FIG. 6 has a support frame member 28 carrying guide rods 29 and supporting a bottom tool 30 having a central hole 31 to receive the valve stem 1. Within a recess 32 in the tool 30, there is located a removable bottom ring 33 of the same diameter as the recess 32. The ring 33 provides a contact region 34 for the valve seating face 6. The valve member is centered in the recess by the contact region 34. Receivable in the recess 32 is a top tool 35 which has a contact ring projection 36 at its lower face which contacts a central region of the head face 5 of the valve member. The top tool 35 is carried by a plate 38 guided on the rods 29 so that the tool 35 can be raised and lowered. Centrally located in the top tool 35 is a means of heating the centre of the head face 5, in this case a laser 37 as described above, but this may be replaced by other suitable heating means such as a flame, a focused high-temperature lamp or a contact heating device.

Static load is applied to the valve member by pressing the top tool 35 downwardly onto the head face 5, using a simple weight or a hydraulic ram (not shown), for example.

The parts 30,33,35 of FIG. 6 are suitably formed of stainless steel, hardened by heat treatment after machining.

The shape of the contact region 34 of the bottom ring 33 is selected in accordance with the pattern of mechanical stress which it is desired to apply to the valve member. The shape shown in FIG. 6 and in FIGS. 7a and 7b (which shows the bottom ring 33) is a rounded annular bead 34 which makes circular line contact with the valve seating face 6 in order to obtain a high stress concentration of that face. A lower stress concentration at the valve seating face 6 is obtained by the alternative bottom ring 33a shown in FIGS. 8a and 8b, which has a frusto-conical face 34a of the same cone angle as the valve seating face 6, so that there is face-to-face contact, as in the apparatus of FIGS. 2 to 5 and in an actual engine.

FIGS. 9a and 9b show another bottom ring 33b for the apparatus of FIG. 6, which provides a three-point contact with the valve seating face 6. Three identical cylindrical tungsten carbide rods 34b are inset in accurately machined grooves in the steel-ring 33b, so that the axes of the rods 34b lie in a common plane parallel to the base of the ring 34b and at 60° to each other. The valve seating face 6 therefore makes contact at one point on each rod 34b. This three-point contact gives higher stress concentration than is given by the rings 33 and 33a.

In a destructive test, the load applied to the valve member by the top tool 35 is increased while being measured, at the same time as thermal stress is applied. In a proof test of valve members, a standard load is applied to each valve member, while a standard quantity of heat is applied by the laser 37. The apparatus of FIG. 6 allows rapid insertion, testing and removal of each valve member of a sequence of valve members.

Calculations made by the present inventors using the FEM (finite element analysis method) technique, have shown that if only mechanical stress is applied to a valve member in the manner shown in FIG. 6 mechanical stress in the underhead 3 exceeds the material strength, causing fracture there. Stress in the seat region 6 becomes critical when thermal stress is applied to the valve head face 5 as well. Therefore in the invention, both thermal stress and mechanical stress are applied.

In an actual engine, the valve member is held by the stem and the seating face 6 makes face contact with the valve seat. An analysis of mechanical stress suggests that maximum stress is at the underhead 3, and that stress at the seating face 6 is low. However in actual engine tests, ceramic valve members have been found to fail at the seating region and not at the underhead. This suggests that for proof testing, attention must be paid particularly to applying stress concentration in the seating region, together with applying thermal stress to the head. The apparatus of FIG. 6 achieves this, without applying load to the valve stem, and stress concentration in the seat can be selected by choice among line contact (as with the bottom ring 33 of FIGS. 7a and 7b), face contact (as with the bottom ring 33a of FIGS. 8a and 8b), and point contact (as with the bottom ring 33b of FIGS. 9a and 9b). At the same time, the apparatus of FIG. 6 also tests the underhead 3.

Alternatively, the apparatus of FIGS. 2 to 5 permits testing of the whole of the valve.

Although cooling is applied to the valve seating face 6 in the apparatus of FIGS. 2 to 5 in which repeated impact load is applied, it is considered that cooling is not always necessary, particularly in the case where a static mechanical load is rapidly, applied, as in the apparatus of FIG. 6. The desired thermal stress is achieved by the rapid application of heat at the centre of the head face 5, which establishes a temperature gradient in the valve head.

FIG. 10 shows an apparatus of the invention for use in applying an impact load to the valve member, in a test. Some parts in this apparatus are similar to those of FIG. 6. In a support frame member 28, which carries guide rods 29, there is a bottom member 30 which in its recess 32 holds a support tool 35 which is similar to the top tool 35 of FIG. 6, but here inverted. The support tool 35 has the ring projection 36 of FIG. 6. At its centre, the support tool 36 receives the laser 37. The valve member rests with its head face 5 on the tool 35.

The guide rods 29 locate a vertically slidable plate 38 which carries an impacter ring 39. Resting on the valve member 1 is a ring 33, similar to the ring 33 of FIG. 6. This ring 33 has a conical face which matches the seating face 6 of the valve member and a contact ring projection 34, as in FIG. 6. The impacter ring 39 and the plate 38 are allowed to fall along the rods 29, from a selected height, onto the ring 33, which transfers the impact to the valve member, to conduct an impact test. The weight of the ring 39 and plate 38 can also be altered, to adjust the impact applied. The shape of the ring 33 can be varied, as shown in FIGS. 7 to 9. The ring 33 ensures correct alignment of the valve member.

As well as for proof testing of valve members which are to be used in actual engines, the apparatus shown in the drawings is also useful for investigations for example of the stress limits of the valve members, for example to investigate how grinding conditions of the valve member, head thickness of the valve member and material characteristics affect the stress limits and the performance of the members.

The invention is not limited to the specific embodiments described above, but modifications and variations are possible within the inventive concept herein set out. The invention is applicable to ceramic members other than valve members, particularly members which are contacted by hot gases or liquids in use or are otherwise subjected to thermal stress, such as flap valve members (which may be used in bypass valves of an exhaust system of an internal combustion engine), other. IC engine parts such as a cylinder head plate, a piston cap, an exhaust port liner and a swirl or precombustion chamber (of a Diesel engine), gas turbine combustion ducts and rings and gas turbine stator blades, and ceramic substrates used in electronic components which are subjected to heating by electronic devices.

What is claimed is:

1. A method of proof-testing a plurality of ceramic engine valve members for quality assurance, wherein each valve member has a stem, a head at one end of the stem, an annular seating face on the side of the head towards the stem and a head face at the side of the head facing away from the stem, the method comprising subjecting each valve member (a) to mechanical stress applied by pressing the seating face against a tool and (b) simultaneously with said mechanical stress, to thermal stress applied by locally heating a central region of the head face.

2. A method according to claim 1 including cooling said seating face of each valve member while applying said mechanical and thermal stresses.

3. A method according to claim 2 wherein the cooling of the seating face is effected by heat transfer to the tool, which is cooled.

4. A method according to claim 1 wherein each valve member is a one-piece member of silicon nitride, shaped by grinding.

5. A method according to claim 1 wherein said mechanical stress is impact stress applied by repeated contact of said tool with said seating face.

6. A method according to claim 1 wherein said mechanical stress is applied by means of a static load.

7. A method according to claim 6 wherein said static load is applied by said tool contacting the seating face and a further tool contacting the head face of the valve member.

8. A method according to claim 1 wherein at least one of said mechanical stress and said thermal stress applied is greater than the corresponding stress expected in normal use of the valve member in an engine.

9. A method according to claim 8 wherein the heating to apply said thermal stress induces a temperature gradient in the valve member greater than that expected in normal use of the valve member in an engine.

10. Apparatus for testing a ceramic engine valve member comprising a tool adapted to contact a predetermined portion of the valve member, means for pressing said tool against the valve member to apply mechanical stress to the valve member, and heating means for local heating a predetermined portion of the valve member to apply thermal stress simultaneously with the application of said mechanical stress, wherein said tool is a striker member and said pressing means includes a holder for the valve member and means for relatively moving said striker member and said holder to cause said striker member to apply impact load to the valve member.

11. Apparatus for testing a ceramic engine valve member comprising a tool having a region shaped and adapted to contact an annular seating face of the valve member, means for pressing said tool against said seating face of the valve member to apply mechanical stress to the valve member, and heating means arranged for locally heating a predetermined portion of a head face of the valve member to apply thermal stress to the valve member simultaneously with the application of said mechanical stress.

12. Apparatus according to claim 11 wherein said tool is adapted to impose, with said pressing means, a static load on said valve member, to apply said mechanical stress.

13. Apparatus according to claim 11 wherein said heating means comprises means for spot-heating of a surface portion of said head face of said valve member.

14. Apparatus according to claim 11 including means for observing a temperature gradient induced in the valve member by said heating means.

15. A method of proof-testing a ceramic engine valve member for quality assurance, wherein the valve member has a stem, a head at one end of the stem, an annular seating face on the side of the head towards the stem and a head face at the side of the head facing away from the stem, the method comprising subjecting the valve member (a) to mechanical stress applied by pressing the seating face against a tool and (b) simultaneously with said mechanical stress, to thermal stress applied by locally heating a region of the head face.

16. The method according to claim 15 wherein the region of the head face is a central region thereof.

17. A method according to claim 15 including cooling said seating face of the valve member while applying said mechanical and thermal stresses.

18. A method according to claim 17 wherein the cooling of the seating face is effected by heat transfer to the tool, which is cooled.

19. A method according to claim 15 wherein the valve member is a one-piece member of silicon nitride, shaped by grinding.

20. A method according to claim 15 wherein said mechanical stress is impact stress applied by repeated contact of the tool with said seating face.

21. A method according to claim 15 wherein said mechanical stress is applied by means of a static load.

22. A method according to claim 15 wherein said static load is applied by the tool contacting the seating face and a further tool contacting the head face of the valve member.

23. A method according to claim 15 wherein at least one of said mechanical stress and said thermal stress applied is greater than the corresponding stress expected in normal use of the valve member in an engine.

24. A method according to claim 23 wherein the heating to apply said thermal stress induces a temperature gradient in the valve member greater than that expected in normal use of the valve member in an engine.

25. Apparatus according to claim 10 wherein said striker member is cooled, so as to effect cooling of the valve member when in contact therewith.

26. Apparatus according to claim 25 wherein said tool is a striker member and said pressing means includes a holder for the valve member and means for relatively moving said striker member and said holder to cause said striker member to apply impact load to the valve member.

27. Apparatus according to claim 26 wherein said striker member is cooled, so as to effect cooling of the valve member when in contact therewith.

* * * * *